United States Patent
Mihalef et al.

(10) Patent No.: US 10,726,546 B2
(45) Date of Patent: Jul. 28, 2020

(54) TISSUE-TO-FLOW IMAGE GENERATION IN MEDICAL IMAGING

(71) Applicant: Siemens Healthcare GmbH, Erlangen (DE)

(72) Inventors: Viorel Mihalef, North Brunswick, NJ (US); Saikiran Rapaka, Pennington, NJ (US); Yefeng Zheng, Princeton Junction, NJ (US); Puneet Sharma, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 145 days.

(21) Appl. No.: 15/963,166

(22) Filed: Apr. 26, 2018

(65) Prior Publication Data
US 2019/0333210 A1 Oct. 31, 2019

(51) Int. Cl.
*G06T 7/00* (2017.01)
*A61B 8/06* (2006.01)
*A61B 8/08* (2006.01)
*A61B 5/00* (2006.01)
*A61B 5/055* (2006.01)
*A61B 6/03* (2006.01)

(52) U.S. Cl.
CPC ............ *G06T 7/0012* (2013.01); *A61B 5/055* (2013.01); *A61B 5/7267* (2013.01); *A61B 6/032* (2013.01); *A61B 8/06* (2013.01); *A61B 8/488* (2013.01); *G06T 2207/10081* (2013.01); *G06T 2207/10084* (2013.01); *G06T 2207/10088* (2013.01); *G06T 2207/20081* (2013.01); *G06T 2207/30104* (2013.01)

(58) Field of Classification Search
CPC ....... A61B 5/055; A61B 5/7267; A61B 6/032; A61B 8/06; A61B 8/488; G06T 2207/10081; G06T 2207/10084; G06T 2207/10088; G06T 2207/20081; G06T 2207/30104; G06T 7/0012
See application file for complete search history.

(56) References Cited

U.S. PATENT DOCUMENTS

| | | | |
|---|---|---|---|
| 2013/0012823 A1* | 1/2013 | Ripoll | A61B 5/021 600/479 |
| 2016/0078668 A1* | 3/2016 | Wong | G06T 15/08 345/424 |
| 2019/0175138 A1* | 6/2019 | Torp | A61B 8/488 |

OTHER PUBLICATIONS

Huo, Yuankai, et al. "Splenomegaly segmentation using global convolutional kernels and conditional generative adversarial networks." Medical Imaging 2018: Image Processing. vol. 10574. International Society for Optics and Photonics, 2018. (Year: 2018).*
Isola, Phillip, et al. "Image-to-image translation with conditional adversarial networks." arXiv preprint (2017).
Itu, Lucian, et al. "A machine-learning approach for computation of fractional flow reserve from coronary computed tomography." Journal of Applied Physiology 121.1 (2016): 42-52.

(Continued)

*Primary Examiner* — Nirav G Patel (57) ABSTRACT

A network is machine trained to estimate flow by spatial location based on input of anatomy information. A medical scan of tissue may be used to generate flow information without the delay or difficulty of performing a medical scan configured for flow imaging or CFD. Anatomy imaging is used to provide flow estimates with the speed provided by the machine-learned network.

18 Claims, 4 Drawing Sheets

(56) References Cited

OTHER PUBLICATIONS

L'ubor Ladick' et al. "Data-driven fluid simulations using regression forests." ACM Transactions on Graphics (TOG) 34.6 (2015): 199.

Retarekar, Rohini, et al. "Stratification of a population of intracranial aneurysms using blood flow metrics." Computer methods in biomechanics and biomedical engineering 18.10 (2015): 1072-1082.

Thomas, James D., and Arthur E. Weyman. "Echocardiographic Doppler evaluation of left ventricular diastolic function. Physics and physiology." Circulation 84.3 (1991): 977-990.

Treuille, Adrien, Andrew Lewis, and Zoran Popović. "Model reduction for real-time fluids." ACM Transactions on Graphics (TOG). vol. 25. No. 3. ACM, 2006.

Watanabe, Hiroshi, et al. "Multiphysics simulation of left ventricular filling dynamics using fluid-structure interaction finite element method." Biophysical journal 87.3 (2004): 2074-2085.

\* cited by examiner

TISSUE-TO-FLOW IMAGE GENERATION IN MEDICAL IMAGING

BACKGROUND

The present embodiments relate to imaging flow in a patient. Across medical imaging modalities, there are a number of technologies that perform flow imaging concurrently with tissue imaging. Phase-contrast magnetic resonance imaging (PC-MRI) provides both flow as well as anatomy data. Doppler ultrasound may be interleaved with B-mode ultrasound to provide both flow and anatomy imaging. Some modalities, like computed tomography (CT) do not produce flow information. While computations fluid dynamic (CFD) may be used to estimate flow from CT data, CFD is time consuming.

Information contained in the flow images or indices of clinical significance derived from the flow images may be used for diagnosis, prevention, treatment and/or intervention planning. Such information can be readily observable from the flow images or could be more deeply embedded as features detectable by more sophisticated algorithms. However, gathering of the flow data may be slow as compared to tissue imaging and may fail for certain patients (e.g. PC-MRI failure where maintaining a breath hold is unfeasible).

SUMMARY

Systems, methods, and instructions on computer readable media are provided for flow estimation based on anatomical information. A network is machine trained to estimate flow by spatial location based on input of anatomy information. A medical scan of tissue may be used to generate flow information without the delay or difficulty of performing a medical scan configured for flow imaging or CFD. Anatomy imaging is used to provide flow estimates with the speed provided by the machine-learned network.

In a first aspect, a method is provided for flow estimation based on anatomical information from a medical imaging system. The medical imaging system scans a region of a patient. The region has tissue and fluid, and the scanning is configured for detecting tissue responses. Flow estimates are generated for the fluid of the region from the tissue responses by a machine-trained image-to-image network for tissue-to-flow conversion. An image from the flow estimates is displayed.

In a second aspect, a medical imaging system is provided for flow estimation based on anatomical information. A medical scanner is configured to scan a volume of a patient and generate the anatomical information from the scan. An image processor is configured to apply a machine-learned network to the anatomical information. The machine-learned network was trained to generate flow information for the volume from the anatomical information. A display is configured to display a medical image from the flow information.

In a third aspect, a method is provided for machine training for flow estimation. A machine learning network arrangement is defined with a generative architecture. A machine trains the machine learning network arrangement with training data having ground truth flow data and having input anatomy data. The neural network as trained is stored.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EMBODIMENTS

Artificial intelligence (AI) provides tissue-to-flow image generation. Flow information (e.g., images and/or hemodynamic indices derived from flow estimates) are provided without the need of flow imaging and without the need for CFD.

Figure 1:
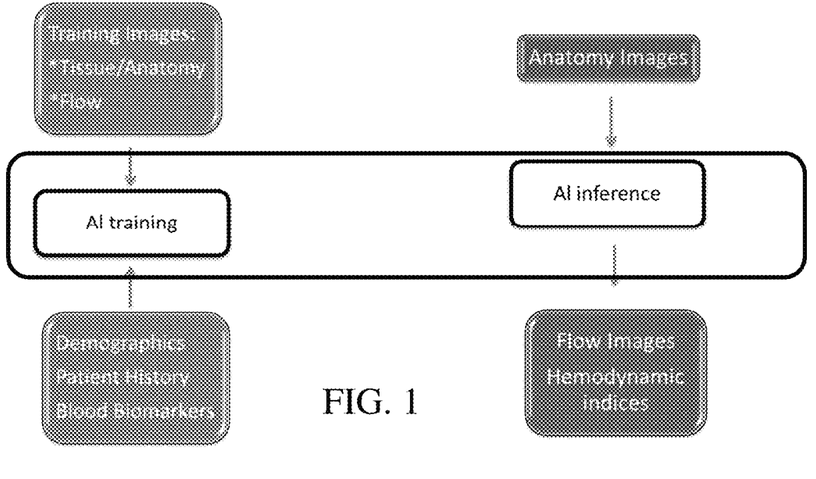
FIG. 1 illustrates one embodiment of machine training and using a machine-learned network to estimate flow from anatomy.

FIG. 1 illustrates an example approach. The left side shows training the AI. A machine learning algorithm is trained to map anatomy or tissue images to corresponding flow images. The input is the anatomy information with the ground truth for training being the flow information. Examples include anatomy and flow from a PC-MRI exam or ultrasound (e.g., B-mode and corresponding Doppler). The training may or may not include temporal information, such as training from anatomy and flow in time sequences. Other inputs, such as demographics, patient history, and/or blood biomarkers, may also be included for training and inference. The right side shows application of the machine-learned network. The AI infers flow data starting from a new (i.e., unseen) set of anatomy data from the same modality. Values for hemodynamic parameters may be inferred and/or derived from the inferred flow data.

The use of AI to infer the flow from anatomy provides accurate flow quickly. As compared to CFD, the machine-learned network is used to provide flow information much more quickly (e.g., in a second verses minutes). As compared to medical imaging of flow, the machine-learned network may be used to estimate flow without requiring a breath hold or having to suffer motion artifacts.

Figure 2:
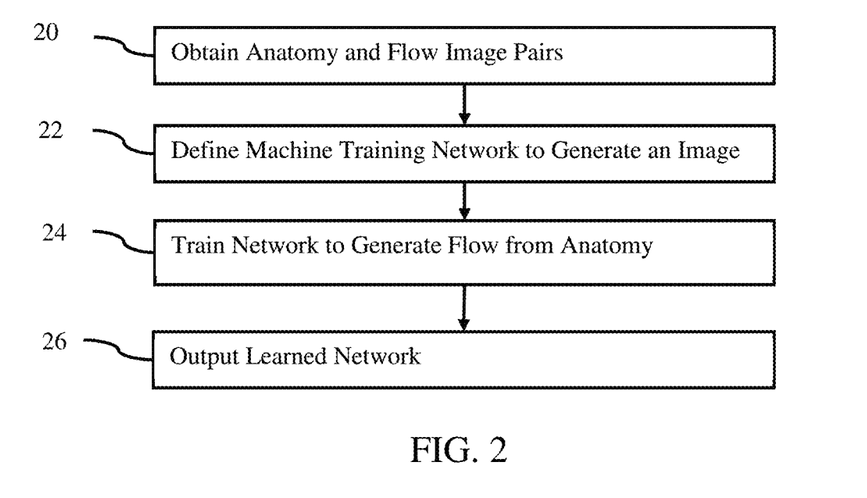
FIG. 2 is a flow chart diagram of one embodiment of a method for machine training for flow estimation based on anatomical data.
Figure 4:
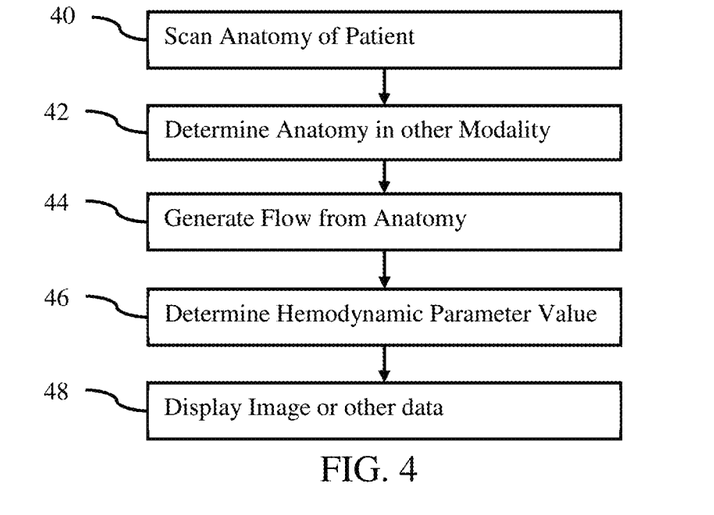
FIG. 4 is a flow chart diagram of one embodiment of a method for flow estimation based on anatomical information from a medical imaging system.

FIGS. 2 and 4 show methods for flow estimation. The method for flow estimation may be a method to learn how to estimate flow from anatomy or may be a method for estimating the flow from anatomy. FIG. 2 is directed to machine training of the network for flow estimation. FIG. 4 is directed to application of a machine-learned network. In both cases, a machine, such as an image processor of a medical imaging system, workstation, computer, or server, implements some or all the acts. The same or different machine is used for training and application. The system of FIG. 6 implements one or both methods in one embodiment, but other systems may be used.

A user may select the image files for application of the learnt network by the processor or select the images from which to learn features and train the network by a processor. Use of the machine allows processing large volumes (e.g., images of many pixels and/or many images) of information that may not be efficiently handled by humans, may be unrealistically handled by humans in the needed time frame, or may not even be possible by humans due to unknown relationships and/or timing. The machine may learn in a way different than a human to estimate flow from anatomy, improving diagnosis or treatment.

The methods are provided in the orders shown (e.g., top to bottom or numerical), but other orders may be provided. For FIG. 2, acts 20 and 22 may be performed in a reverse order. For FIG. 4, acts 46 and 48 may be performed in a reverse order.

Additional, different or fewer acts may be provided. For example, act 26 of FIG. 1 is not provided. As another example, acts 42, 46, and/or 48 of FIG. 4 are not provided. In yet other examples, acts for capturing images, configuring systems, and/or acts using output information are provided.

FIG. 2 shows a method for flow estimation (i.e., generating values for flow) through learning by an image processor or other machine. Machine learning learns to estimate flow from anatomy (e.g., tissue-to-flow image generation). The machine learning trains to predict a spatial distribution of flow (e.g., velocity) from a spatial distribution of tissue.

In act 20, training data is obtained. Images of a same type of object (e.g., heart) are obtained. The images are obtained by data transfer, capture, and/or loading from memory. Any number of images of a same type of object is obtained, such as tens or hundreds of images of the object. The images are obtained with a same type of scanner, whether being from a same scanner or different scanners of the same type (e.g., using an MR scanner or scanners). The object as occurring in many different patients is included in the collection of images. Where the object occurs with different backgrounds, the images are of the object in the various backgrounds or with the backgrounds masked.

In one embodiment, the images are of the heart. In other embodiments, the images are of other parts of the body, such as the torso, head, or other location in patients with both tissue and fluid (e.g., blood, urine, fluid in the lungs, or fluid in the intestinal path). The object of interest in a medical image may be an organ (e.g., whole heart), part of an organ (e.g., left ventricle or other heart chamber), a cyst, a tumor, a vessel, or other tissue structure.

In one embodiment, the images are captured using MR scanners. For example, gradient coils, a whole-body coil, and/or local coils generate a pulse sequence in a magnetic field created by a main magnet or coil. The whole-body coil or local coils receive signals responsive to the re-orientation of molecules shifted due to the pulse sequence. In other embodiments, the images are captured using x-ray, fluoroscopy, angiography, ultrasound, or other modality capable of providing both tissue and flow information. In yet other embodiments, multi-modality imaging provides tissue information from one modality and flow information from another modality for a same patient at a same or similar (e.g., within minutes) time. Many samples of tissue and corresponding flow are acquired.

The obtained images may be scan data to be used to generate an image on a display, such as a medical image being scan data from medical imaging. The obtained images may be data being processed to generate an image, data formatted for display, or data that has been used to display. Scan data may be data with no or some image processing. For example, a displayed image may represent scan data after image processing.

The images represent volumes. Three-dimensional datasets are obtained. Values for different locations distributed in three dimensions (e.g., N×M×O where N, M, and O are integers greater than 1) are used. In alternative embodiments, two-dimensional datasets representing planes are obtained. The images represent the tissue and/or flow at a same time. In other embodiments, sequences of images representing the same tissue and/or flow over time are acquired for training.

The medical images are used for training in act 24. The medical images may be used as received or may be pre-processed, such as segmented, filtered (e.g., noise removal), masked (e.g., removing background information), and/or having geometric features identified (e.g., boundaries, centerlines, and/or hydraulic diameters). In one embodiment of pre-processing, the received images are normalized. Since different settings, imaging systems, patients being scanned, and/or other variations in acquiring images may result in different offsets and/or dynamic ranges, normalization may result in more uniform representation of the object. Any normalization may be used, such as setting a maximum value to 1 with all other values linearly scaled between 0 and 1. Each volumetric scan or medical image is individually normalized.

The training data includes a ground truth indication of the object. In this case, the ground truth is the flow. Flow may be a magnitude of response from fluid, a velocity, an acceleration, a variance, or other characterization of fluid or fluid movement. For ultrasound, the flow information may be Doppler estimates. For MR, the flow information may be phase contrast (PC-MRI) flow values. The flow information may be non-directional or directional. For example, the flow is signed to indicate one-dimensional direction, such as with ultrasound. As another example, the flow is a 3D vector for each location, such as provided with PC-MRI.

Other ground truth data may be provided, such as values for flow parameters (e.g., FFR) and/or outcome predictions. For example, the ground truth includes the therapy that was chosen for the patient for each sample, along with the recorded outcome at one or more temporal points (for instance, 30 days, 90 days, etc.), including the occurrence or lack thereof of adverse events. The machine may learn to both output flow as well as an outcome prediction.

The training data includes input samples for each of the output (ground truth) samples. The input samples are tissue or anatomy images. The response from anatomical structure rather than fluid is represented. While fluid response may cause an artifact or occur, the values of the data are primarily responsive at each location to tissue, bone, or other anatomical structure and not fluid. In ultrasound, the B-mode, harmonic, Doppler tissue, or other tissue-based detection is used. For MR, tissue-based detection is used. Other input information, such as demographics (e.g., group membership), patient information (e.g., history, age, sex, weight, body-mass-index, body surface area, heart pressure, and/or heart rate), blood biomarkers, and/or genetic information, may be provided as input of the samples.

In act 22, a machine learning network arrangement is defined. The definition is by configuration or programming of the learning. The number of layers or units, type of learning, and other characteristics of the network are controlled by the programmer or user. In other embodiments, one or more aspects (e.g., number of nodes, number of layers or units, or type of learning) are defined and selected by the machine during the learning.

The machine learning network is an image-to-image network. Any machine training architecture for outputting a spatial distribution from an input spatial distribution may be used. For example, U-net is used. A convolutional-to-transposed-convolutional network is used. One segment of layers or units applies convolution to increase abstractness or compression. The most abstract feature values are then output to another segment. The other segment of layers or units then applies transposed-convolution to decrease abstractness or compression, resulting in outputting of a segmentation or indication of class membership by location. An encoder (convolutional) and decoder (transposed-convolutional) network forms a "U" shape with one vertical being encoding, another vertical being decoding, and the connection between being passing features at a greatest level of compression or abstractness from the encoder to the decoder. Any now known or later developed U-net architectures may be used. Other fully convolutional networks may be used.

In one embodiment, the network arrangement is a neural network for deep learning. For example, a generative network or architecture formed by convolutional and/or deconvolutional layers is used. In one embodiment, a generative adversarial network is used. Other network arrangements may be used, such as a support vector machine.

Deep architectures include convolutional neural network (CNN) or deep belief nets (DBN), but other deep networks may be used. CNN learns feed-forward mapping functions while DBN learns a generative model of data. In addition, CNN uses shared weights for all local regions while DBN is a fully connected network (i.e., having different weights for all regions of an image). The training of CNN is entirely discriminative through back-propagation. DBN, on the other hand, employs the layer-wise unsupervised training (e.g., pre-training) followed by the discriminative refinement with back-propagation if necessary.

The network is defined as a plurality of sequential feature units or layers. Sequential is used to indicate the general flow of output feature values from one layer to input to a next layer. The information from the next layer is fed to a next layer, and so on until the final output. The layers may only feed forward or may be bi-directional, including some feedback to a previous layer. The nodes of each layer or unit may connect with all or only a sub-set of nodes of a previous or subsequent layer or unit.

Rather than pre-programming the features and trying to relate the features to attributes, the deep architecture is defined to learn the features at different levels of abstraction based on an input image or scan data with or without pre-processing. The features are learned to reconstruct lower level features (i.e., features at a more abstract or compressed level). For example, features for reconstructing an image are learned. For a next unit, features for reconstructing the features of the previous unit are learned, providing more abstraction. Each node of the unit represents a feature. Different units are provided for learning different features.

Within a unit or layer, any number of nodes is provided. For example, 100 nodes are provided. Later or subsequent units may have more, fewer, or the same number of nodes. In general, for convolution, subsequent units have more abstraction. For example, the first unit provides features from the image, such as one node or feature being a line found in the image. The next unit combines lines, so that one of the nodes is a corner. The next unit may combine features (e.g., the corner and length of lines) from a previous unit so that the node provides a shape or building indication. For transposed-convolution to reconstruct, the level of abstraction reverses. Each unit or layer reduces the level of abstraction or compression.

The features of the nodes are learned by the machine using any building blocks. For example, auto-encoder (AE) or restricted Boltzmann machine (RBM) approaches are used. AE transforms data linearly, and then applies a non-linear rectification, like a sigmoid function. The objective function of AE is the expected mean square error between the input image and reconstructed images using the learned features. AE may be trained using stochastic gradient descent or other approach to learn, by the machine, the features leading to the best reconstruction. The objective function of RBM is an energy function. Exact computation of the likelihood term associated with RBM is intractable. Therefore, an approximate algorithm, such as contrastive-divergence based on k-step Gibb sampling or other, is used to train the RBM to reconstruct the image from features.

Training of AE or RBM is prone to over-fitting for high-dimensional input data. Sparsity or denoising techniques (e.g., sparse denoising AE (SDAE)) are employed to constrain the freedom of parameters and force learning of interesting structures within the data. Enforcing sparsity within hidden layers (i.e., only a small number of units in hidden layers are activated at one time) may also regularize the network. In other embodiments, at least one unit is a convolution with ReLU activation or is a batch normalization with a ReLU activation followed by a convolution layer (BN+LeakyRU+convolution). Different units may be of the same or different type.

In act 24, a machine (e.g., image processor, workstation, computer, or server) trains the network arrangement with the training data having ground truth flow. The neural network is trained using the medical images of the tissue or anatomy and the ground truth flow for fluid in or by the tissue or anatomy. Machine learning is performed to train the various units using the defined architecture. The features (e.g., convolution kernels, transposed-convolution kernels, and max pooling connections) that are determinative or map to the ground truth are learned. The features providing the desired result or detection of the object are learned. Alternatively or additionally, the relationship of input features (e.g., Haar wavelets, gradients, centerlines, segmentation, or other derivations from the anatomy or tissue images) to the ground truth are learned. Rather than or in addition to learning filter kernels for convolution, the relationship of input feature vectors from tissue or anatomy to output flow estimates is learned. The training may learn the relationship of other data, such as demographics, patient information, blood biomarkers, and/or genetic information, to the estimated flow output.

The results relative to the ground truth and the error for reconstruction for the network are back-projected to learn the features that work best. In one embodiment, a L2-norm loss is used to optimize the network. Other error functions may be used. In one embodiment, the weights of the network are randomly initialized, but another initialization may be used. End-to-end training is performed, but one or more features may be set. Batch normalization, dropout, and data augmentation are not used, but may be. The optimization is with the RMSprop optimizer, but other optimization functions (e.g., Adam, SGD, etc.) may be used. During the optimization, the different distinguishing features are learned. The features providing an indication of flow given input medical image of anatomy or tissue are learned.

The network learns to output flow in response to input of anatomy. For example, the network learns to output Doppler velocity estimates by location based on input B-mode images. As another example, the network learns to output PC-MRI flow measures based on input tissue response to MR. The output is for spatially distributed locations, such as outputting flow values for 3D locations based on input tissue or anatomy data for the same or different 3D locations.

Once trained, the model may be applied to estimate flow from input tissue information. In other embodiments, the training continues. The network is periodically updated. For example, online or other updated learning is performed. As new samples are acquired, the learning is repeated in total or to incorporate the further training data.

The many samples in the training data are used to learn to output flow imaging from anatomy imaging. The machine learning model is trained to learn the correspondence between the parameters of the anatomy or tissue images and the flow image data. The machine learning model may be trained to provide flow imaging data over a sequence, such as based on input of a sequence of anatomy or tissue images for a patient. The flow data output may be directional or only magnitude without direction.

In act 16, the machine outputs a trained network. The machine-learned network is an image-to-image network incorporating the deep learned features for the various units and/or layers of the network and/or the relationships of input features to the output. The collection of individual features forms a feature or feature set for estimating flow from anatomy. For a convolutional neural network, the features are provided as nodes of the feature units in different levels of abstraction or compression. The nodes define convolution kernels trained to extract the features.

Once trained, a matrix, kernels, or other trained network is output. The data represents the trained architecture. The machine-learned network includes definitions of convolution kernels, links, weights, pooling, and/or other characteristics of the network trained to estimate spatial distribution of flow. Alternatively, separate matrices or network representations are used for any of the nodes, units, layers, network, and/or detector. For example, directional or vector flow is represented by x, y, and z components. Separate or interconnected networks are trained to estimating each of the components as output.

The machine-learned detector is output to a network or memory. For example, the neural network as trained is stored in a memory for transfer and/or later application.

Using the features, the machine-learned network may estimate the flow from one or more input images (e.g., estimating flow over time for an input series of medical images for a patient). Once the network is trained, the network may be applied. The network with defined or learnt features is used to extract from previously unseen input images with or without other inputs (e.g., patient information). The machine-learned network uses extracted features from the image with or without other information to estimate the flow.

Figure 3:
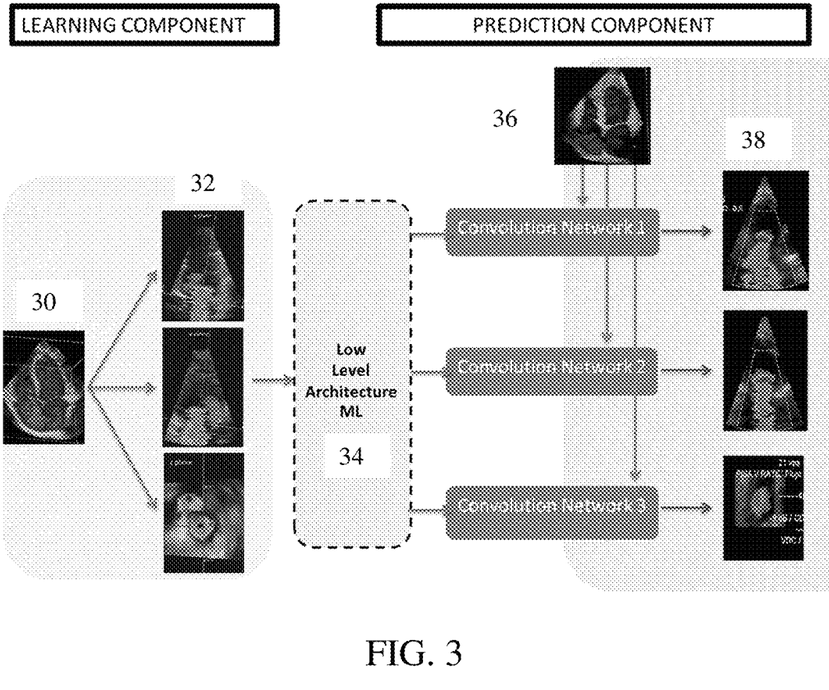
FIG. 3 illustrates an embodiment for learning to predict and prediction of flow from anatomy.

FIG. 3 shows an example embodiment for PC-MRI. For the learning component, many samples of PC-MRI data are acquired. The image 30 is an example tissue image shown in 2D but representing 3D spatial distribution. Images 32 are x, y, and z components of 3D velocity vectors from the PC-MRI data for the tissue image 30. In training, a low-level architecture 34 is used for machine learning. The low-level architecture 34 uses input features extracted from the image 30 and other images at a low level, such as gradient or Haar wavelets. Other low-level architectures may use a deep learning approach where the image 30 without extracting features is input. In alternative embodiments, higher level features are used.

The result of the training provides three networks or one network with three outputs. Each convolutional network receives an input anatomy or tissue image 36 and outputs the corresponding x, y, or z components 38 of the flow direction. Each component is a magnitude or amount of the flow in that direction. A 3D vector is output for each location but other coordinate systems and corresponding representation of direction and magnitude of flow may be used. The framework of FIG. 3 provides for tissue-to-flow (TTF) image generation, illustrated for the specific case of PC-MRI data. A same or similar arrangement may be used for ultrasound, such as providing the flow information as scalar and sign components.

FIG. 4 is a flow chart diagram of one embodiment for flow estimation based on anatomical information from a medical imaging system. The machine-learned network is applied to estimate the flow or provide a flow image.

Figure 6:
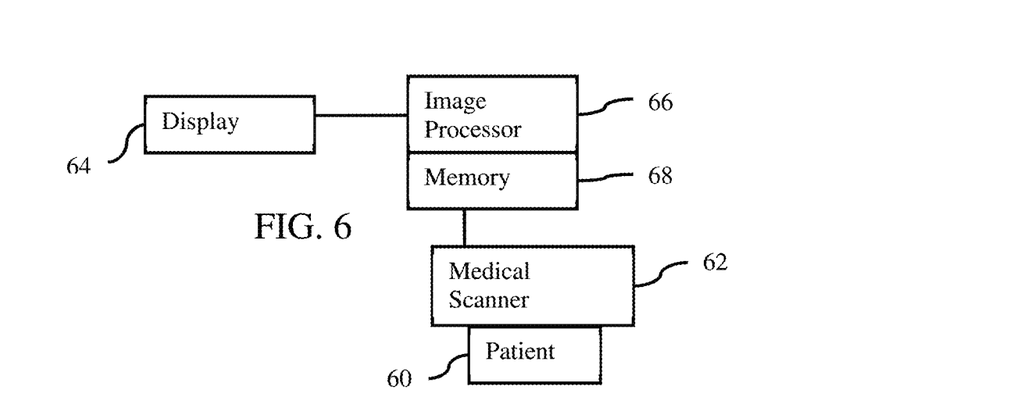
FIG. 6 is a block diagram of one embodiment of a system for flow estimation based on anatomical information.

The same image processor or a different image processor than used for training applies the learnt features and/or network. For example, the network architecture, learnt weights, and learnt kernels are transmitted from a graphics processing unit used to train to a medical scanner, medical server, or medical workstation. An image processor of the medical device applies the machine-learned network. For example, the medical imaging system of FIG. 6 is used. In one embodiment, the medical scanner or a work station at a same facility as the medical scanner applies the machine-learned network. In another embodiment, a server remote from the medical scanner and/or remote from a facility with the medical scanner applies the machine-learned network, such as providing flow imaging as a service based on input of a tissue image from a client.

In act 40, the image processor receives an anatomy image or a sequence of anatomy images. The images are from a scan of a patient. For example, an MR imaging system scans the heart of a patient (e.g., torso, cardiac or heart scan). The resulting scan data is received from or by the MR system. The receipt is by scanning the patient. Alternatively, the receipt is by receiving from a network interface. In other embodiments, receipt is by loading from memory.

The tissue response from the scan is detected as the image for input to the network. While the scan region of the patient may include both tissue and fluid, the imaging system is configured for tissue detection. The response from tissue is detected by scanning. For each location represented in the image, the value represents response from tissue or anatomy and no or less response from fluid. The imaging system is configured for anatomy or tissue imaging rather than for flow imaging. The image is acquired without scanning for flow. Flow imaging by scanning in a configuration for detecting flow may be avoided.

The type or modality of medical imaging system used for scanning is the same type or modality of medical imaging system used to produce the tissue images for training. The same or different scanner may be used, but the same physics (e.g., x-ray, ultrasound, or magnetic resonance) is used. For example, an MR or ultrasound scanner scans for tissue detection.

The scan is a 2D or 3D scan. For example, a frame of scan data is acquired as an image representing a planar region of the patient or a volume of the patient (e.g., multiple stacked planes or slices). The tissue response from two or three spatial dimensions is detected by scanning.

The received medical image may be pre-processed, such as normalized, filtered, noise removed, masked, geometric features identified, and/or segmented in a same way as the training medical images. The received medical image or images are to be used to estimate flow from the tissue information.

In optional act 42, the image processor determines further tissue responses. In this optional approach, the tissue responses from scanning are used to estimate other tissue responses. For example, computed tomography (CT) is used to detect tissue and may not have the capability of detecting flow. The CT data for tissue responses from different locations is used to estimate tissue responses from a different modality, such as MR. Since MR may detect flow response, training data is available to train flow estimation from tissue response. By converting the CT tissue responses to MR tissue responses, the flow estimation may be performed. Flow estimation is provided for CT tissue responses.

A modality operating with one type of physics (e.g., MR, ultrasound, or x-ray) may be used to scan the patient. The image processor applies a machine-learned network or other conversion to generate tissue responses for a different modality with a different type of physics. The machine-learned network is an image-to-image network with a same, similar, or different architecture used for learning to estimate flow from tissue. For example, the machine-learned network is a fully convolutional neural network, generative network, and/or generative adversarial network trained for tissue-to-tissue conversion between modalities of medical imaging. Using multi-modality scanning, tissue response from different modalities is acquired for training.

The tissue-to-tissue conversion maps from a different anatomy modality to the modality for which the AI is trained to estimate flow (e.g. CT to MR anatomy). The other machine-learned network for flow estimation predicts the flow from the converted tissue response. This intermediate modality mapping allows for flow estimation where the patient is scanned with a modality not having a corresponding flow detection capability.

Figure 5:
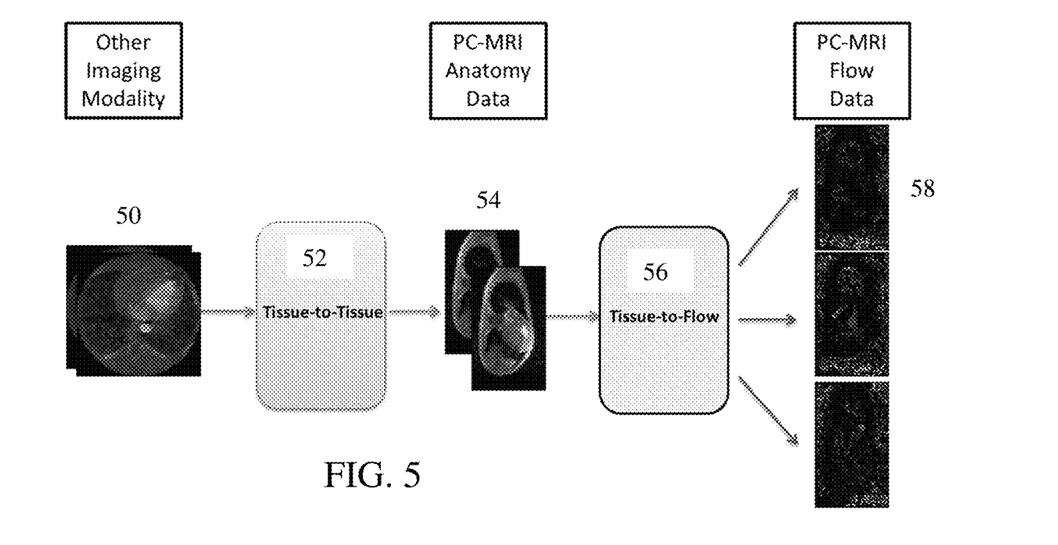
FIG. 5 illustrates an embodiment for flow estimation based on anatomy information from a different modality.

FIG. 5 shows an example. The 3D image data 50 is from one modality, such as CT. The tissue-to-tissue conversion 52 is performed by inputting the 3D image data 50 to the machine-learned network. The resulting tissue responses 54 represent tissue response in a different modality (e.g., PC-MRI). These tissue responses 54 in 3D are input for tissue-to-flow conversion 56. The tissue-to-flow conversion 56 is performed by inputting the tissue responses from the appropriate modality to the machine-learned network for estimating flow for that modality. The resulting flow estimates 58 are output, such as x, y, and z components for PC-MRI flow data. Flow is estimated for a different tissue imaging modality using a mapping of anatomical images of one modality (e.g., CT) to anatomical images of another modality (e.g., MR anatomical images).

In act 44, the image processor generates flow from anatomy. Scalar values for locations distributed in two or three dimensions representing tissue response or features derived therefrom are input to the machine-learned network and scalar or vector values for flow or other fluid response are output. For example, a MR-based tissue or anatomy image is input, and a MR-based flow image (e.g., PC-MRI) is output. As another example, an ultrasound B-mode or harmonic B-mode image is input, and a Doppler velocity and/or energy image is output. The network does not convert the physics, but instead converts from anatomy to fluid. In other embodiments, the conversion from anatomy to fluid also includes a conversion of physics (e.g., combining the networks 52 and 56 of FIG. 5 into one network, such as to scan with CT and output PC-MRI flow.

The machine-learned network for tissue-to-flow conversion is applied. Any inputs for which the network is trained to use are applied as an input feature vector, such as pre-processed image or scan data with or without other information (e.g., demographics, patient information, and/or blood biomarkers). In some embodiments, a sequence of images is input, such as scan data acquired at different times throughout a cardiac or breathing cycle (e.g., 10-20 frames of data over one or more heart cycles).

By applying the image-to-image network, such as a generative adversarial network trained to convert anatomy information to fluid information, the conversion is performed. For example, the trained convolution units, weights, links, and/or other characteristics of the network are applied to the scan data or derived feature values to extract the corresponding features through a plurality of layers and output the estimates of flow. The features of the input images are extracted from the images. Other more abstract features may be extracted from those extracted features using the architecture. Depending on the number and/or arrangement of units or layers, other features are extracted from features.

In one embodiment, the machine-learned network is a fully convolutional network, such as a convolutional-to-transposed-convolutional network. The machine-learned network may be a U-net encoder-decoder trained for detection of the heart region or other tissue (e.g., soft tissue or muscle) region with fluid. Multiple levels of feature compression or abstraction are provided, such as four. The encoder segment has a plurality of convolutional layers with increasing feature compression or abstraction, and the decoder segment has a plurality of transposed-convolutional layers with decreasing feature compression or abstraction.

The trained network is configured by the machine training to output estimates of flow at a resolution of the input medical images or scan data or a different resolution where the ground truth flow data was at a different resolution than the input samples. The output is flow at a given time or a sequence of flow values representing flow over time. The output flow is a scalar or magnitude. In other embodiments, directional (e.g., 1D or 3D vectors) flow values are output. By application, the image processor generates flow estimates for the fluid of the region from the tissue responses. The machine-learned model is used to generate directional or other flow information starting from new tissue imaging slices or data sets.

In act 46, the image processor determines other information from the flow estimates. Alternatively, the network is trained to output the other information based on the input with or without also outputting spatially distributed flow estimates.

In one embodiment, values for one or more hemodynamic parameters are determined from the output flow estimates. The value for any hemodynamic parameter may be determined, such as any hemodynamic indices based on the generated directional flow images. These parameters include cardiac-specific or vessel specific indices. Cardiac specific indices may include volumetric and flow curves, diastolic flow wave front velocity, peak velocity of early rapid filling, isovolumic relaxation time (IVRT), maximal diastolic acceleration and deceleration rates, velocity time integral of the E wave, ventricular residence time distribution, or others. Vessel specific indices may include pressure drop computed from velocity for stenotic regions, wall shear stress (WSS)

and related measures like time averaged WSS (TAWSS) or oscillatory shear index (OSI), inflow concentration index (ICI), relative residence time (RRT), kinetic energy ratio (KER), or others.

In additional or alternative embodiments, the image processor determines risk or prediction. The flow estimates are used to select a therapy, such as selecting based on predicted outcomes of different therapy choices. Any predictive technique may be used, such as applying the flow estimates or features derived therefrom into a machine-learned network for predicting outcome or for providing risk for one or more therapies. The outputs from the tissue-to-flow conversion network are inputs into a higher-level machine learning system for patient risk assessment and scoring, outcome assessment, and/or follow-up scheduling.

In another example, the flow estimates or information derived therefrom are used to identify similar patients. A database of previously treated or diagnosed patients is searched using the flow estimates with or without other information (e.g., patient information) to find any number of similar patients. Any measure of similarity may be used. The outcomes for the similar patients may be used to select a therapy for a current patient.

In act 48, the image processor generates an image or images. The image is output to a display, into a patient medical record, and/or to a report. The image is displayed.

The image is generated from the flow estimates. In one embodiment, the flow estimates represent a 3D distribution of locations. This 3D flow data is rendered to a display image. Any 3D rendering may be used, such as volume, surface, maximum intensity, alpha blending, or path tracing. The 3D data is rendered to a 2D display image. The image represents the distribution of flow from a given camera position. For a 2D distribution of flow, a 2D image may be generated. Color may be used to distinguish direction and/or magnitude. Brightness or intensity may be used for magnitude. Static or time-varying velocity vector magnitude visualization is provided using volumetric rendering or other visualization methods.

In another embodiment, the image is generated as a vector field visualization. A spatial representation of the flow estimates for the scan region of the patient is displayed. The image processor generates arrows or other graphics to represent the flow direction and magnitude in at least two directions. An image with color, brightness, or grayscale modulated by the flow estimates is overlaid with the graphics. Alternatively, an image of anatomy or tissue is overlaid by the graphics from the flow estimates. Static or time-varying velocity vector fields visualization using arrows or other graphics is output.

In yet another embodiment, the displayed image is of or includes an annotation. Any annotation may be used, such as the value of a hemodynamic parameter for the region of the patient, a predicted risk, and/or a recommended therapy. The image with the annotation may or may not also include a spatially distributed representation of the flow and/or anatomy.

Since the flow estimates are determined by application of a machine-learned network, the flow is estimated within a second or seconds. As compared to computational fluid dynamics, the flow estimates are generated more quickly. The image processor operates more efficiently to determine the flow. This allows imaging of flow during a therapy or diagnostic procedure. If a procedure is performed, the intra-procedural tissue image information is used to obtain more accurate, real-time predictions of the flow. This may be especially useful if the patient state has changed since the pre-procedure imaging and/or if the pre-procedure imaging resolution is poorer than the intra-procedure image quality.

FIG. 6 shows a medical imaging system for flow estimation based on anatomical information. The medical imaging system includes the display 64, memory 68, and image processor 66. The display 64, image processor 66, and memory 68 may be part of the medical scanner 62, a computer, server, or other system for image processing medical images from a scan of a patient. A workstation or computer without the medical scanner 62 may be used as the medical imaging system. Additional, different, or fewer components may be provided, such as including a computer network for remote flow image generation of locally captured scans or for local flow image generation from remotely captured scans. The network is applied as a standalone application on the workstation or a local device or as a service deployed on network (cloud) architecture.

The medical imaging system is for training, such as using images from the memory 68 and/or medical scanner 62 as input samples and corresponding ground truth. Alternatively, the medical imaging system is for application of the machine-learned network trained to convert tissue to flow.

The medical scanner 62 is a medical diagnostic imaging system configured to scan a volume of a patient and generate anatomical information from the scan. In one embodiment for application of the machine-learned network, the medical scanner 2 is an MR system configured for tissue scanning, such as MR without performing the flow scanning. A main magnet or coil generates a substantially uniform magnetic field through the patient 60. Gradient coils, local coils, and/or a whole-body coil generate a pulse sequence to shift spin axes of molecules in the patient away from the uniform magnetic field lines. The local coils and/or whole-body coil detect radio frequency emissions caused by the relaxation of the spin axes of the molecules returning to the magnetic field lines. This k-space data is reconstructed into an object or spatial domain using Fourier processing. The resulting scan data represents tissue response from the cardiac region of the patient. The pulse sequence may be repeated or continues to obtain scan data representing the cardiac region over time. Any MR cardiac imaging pulse sequence or scanning may be used.

In another embodiment, the medical scanner 62 is an ultrasound scanner. Transmit and receive beamformers use an ultrasound transducer to acoustically scan a volume of the patient. For network application, the transmit acoustic energy is formatted for tissue (e.g., B-mode) scanning, such as having a scan pattern and pulses for detecting intensity of return. The received signals are applied to a detector for tissue response, such as a B-mode detector.

In yet another embodiment, the medical scanner is a CT scanner. A gantry moves an x-ray source and a detector about a patient. A plurality of projections is formed. Using computed tomography, the tissue response for various spatial locations in the patient is determined. The resulting CT data represents the density of the tissue. Other medical scanners may be used instead, such as positron emission tomography, x-ray, angiography, fluoroscopy, or single photon emission computed tomography.

To avoid complications for scanning for flow, the medical scanner 62 is configured to generate anatomical information without flow estimation from the scan. For example, the MR pulses used to capture flow are not used in the MR scan. As another example, the extra acoustic pulses to the same locations to measure Doppler shift for ultrasound Doppler flow or color imaging are not performed. In alternative embodiments, flow imaging is performed for comparison or combination with flow estimated by the machine-learned network from the tissue information.

The image processor 66 is a control processor, general processor, digital signal processor, three-dimensional data processor, graphics processing unit, application specific integrated circuit, field programmable gate array, digital circuit, analog circuit, combinations thereof, or other now known or later developed device for processing medical image data. The image processor 66 is a single device, a plurality of devices, or a network. For more than one device, parallel or sequential division of processing may be used. Different devices making up the image processor 66 may perform different functions, such as applying the machine-learned network to estimate flow and a separate device for generating an image based on the estimated flow. In one embodiment, the image processor 66 is a control processor or other processor of a medical diagnostic imaging system, such as the medical scanner 62. The image processor 66 operates pursuant to stored instructions, hardware, and/or firmware to perform various acts described herein, such as controlling scanning, preprocessing scan or image data for tissue responses, estimating flow from the tissue responses, and/or generating an output image showing flow.

The image processor 66 is configured to train a machine learning architecture. Based on a user provided or other source of the network architecture and training data, the image processor 66 learns features for an encoder and a decoder or other network parts to train the network. The result of the training is a machine-learned network for flow estimation from input anatomy values.

Alternatively or additionally, the image processor 66 is configured to apply one or more machine-learned networks. For example, an image-to-image network is applied to convert tissue information from one modality into tissue information from another modality (e.g., convert CT data to MR data representing tissue). In another example, the image processor 66 applies an image-to-image network to convert tissue information to flow information. The machine-learned generative network is applied to anatomical information. Based on the previous training, the network generates flow information in response to application of the anatomical information.

The image processor 66 may be configured to output an image showing spatial distribution of the flow. A sequence of images showing the spatial distribution of the flow over time may be output. In other embodiments, the spatial distribution is used to calculate a value for a quantification. The value is output in an image. Any of the images may or may not also include anatomical information, such as an image of tissue overlaid with flow information for some spatial locations.

The display 64 is a CRT, LCD, projector, plasma, printer, tablet, smart phone or other now known or later developed display device for displaying the output, such as a flow image or combination flow and anatomy image. The display 64 displays a medical image generated from the flow information.

The instructions, medical images, network definition, features, machine-learned network, outputs, and/or other information are stored in a non-transitory computer readable memory, such as the memory 68. The memory 68 is an external storage device, RAM, ROM, database, and/or a local memory (e.g., solid state drive or hard drive). The same or different non-transitory computer readable media may be used for the instructions and other data. The memory 68 may be implemented using a database management system (DBMS) and residing on a memory, such as a hard disk, RAM, or removable media. Alternatively, the memory 68 is internal to the processor 66 (e.g. cache).

The instructions for implementing the training or application processes, the methods, and/or the techniques discussed herein are provided on non-transitory computer-readable storage media or memories, such as a cache, buffer, RAM, removable media, hard drive or other computer readable storage media (e.g., the memory 68). Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU or system. Because some of the constituent system components and method steps depicted in the accompanying figures may be implemented in software, the actual connections between the system components (or the process steps) may differ depending upon the manner in which the present embodiments are programmed.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for flow estimation based on anatomical information from a medical imaging system, the method comprising:

scanning a region of a patient by the medical imaging system in three dimensions, the region having tissue and fluid, and the scanning being configured for detecting tissue responses, the tissue responses representing the region in three dimensions;

generating flow estimates for the fluid of the region from the tissue responses in three dimensions, the flow estimates generated by a machine-trained image-to-image network for tissue-to-flow conversion; and displaying a three-dimensional rendering from the flow estimates.

2. The method of claim 1 wherein scanning comprises scanning with the medical imaging system comprising a magnetic resonance or ultrasound scanner, and wherein generating the flow estimates comprises generating phase contrast or Doppler estimates by the machine-trained image-to-image network.

3. The method of claim 1 wherein generating comprises inputting the tissue responses to the machine-trained image-to-image network.

4. The method of claim 1 wherein generating comprises inputting features derived from the tissue responses to the machine-trained image-to-image network.

5. The method of claim 1 wherein the medical imaging system comprises a first modality;

wherein scanning comprises detecting the tissue responses with a physics of the first modality;
further comprising:
determining tissue responses for physics of a second modality different than the physics of the first modality, the determining being by another machine-trained image-to-image network for tissue-to-tissue conversion between the first and second modalities;
wherein generating the flow estimates comprises generating from the tissue responses for the physics of the second modality.

6. The method of claim 5 wherein the first modality comprises computed tomography, and wherein the second modality comprises magnetic resonance, and wherein generating the flow estimates comprises generating phase-contrast estimates.

7. The method of claim 1 wherein generating the flow estimates comprises generating the flow estimates as magnitude of flow.

8. The method of claim 1 wherein generating the flow estimates comprises generating the flow estimates as directional flow estimates.

9. The method of claim 1 further comprising determining a value of a hemodynamic parameter from the flow estimates, and wherein displaying the three-dimensional rendering comprises displaying the value of the hemodynamic parameter for the region of the patient.

10. The method of claim 1 wherein displaying the three-dimensional rendering comprises displaying a spatial representation of the flow estimates for the region of the patient.

11. The method of claim 1 wherein scanning comprises scanning for the tissue response without scanning for fluid response.

12. A medical imaging system for flow estimation based on anatomical information, the medical imaging system comprising:
a computed tomography system configured to scan a volume of a patient and generate computed tomography data representing the anatomical information from the scan;
an image processor configured to apply a first machine-learned network trained to generate magnetic resonance information from the computed tomography data and apply a second machine-learned network to the magnetic resonance information, the second machine-learned network having been trained to generate flow information for the volume from the magnetic resonance information;
a display configured to display a medical image from the flow information.

13. The medical imaging system of claim 12 wherein the second machine-learned network comprises an image-to-image network.

14. The medical imaging system of claim 12 wherein the second machine-learned network comprises a generative network having been trained with deep learning.

15. The medical imaging system of claim 12 wherein the medical scanner is configured to generate the anatomical information without flow estimation from the scan.

16. A method for machine training for flow estimation, the method comprising:
defining a machine learning network arrangement with a generative architecture;
training, by a machine, the machine learning network arrangement with training data having ground truth flow data and having input anatomy data; and
storing the machine learning network as trained.

17. The method of claim 16 wherein training comprises training with the flow data comprising ultrasound or magnetic resonance flow data representing flow in a region for each of a plurality of samples and with the anatomy data comprising ultrasound or magnetic resonance anatomy data representing anatomy in the region for each of the plurality of samples.

18. The method of claim 16 wherein training comprises training the machine learning network to output flow in response to input of anatomy.

* * * * *